United States Patent
Bowers et al.

(10) Patent No.: US 8,119,065 B2
(45) Date of Patent: *Feb. 21, 2012

(54) ACTIVE SAMPLER FOR DETECTING CONTAMINANTS IN LIQUIDS

(75) Inventors: William D. Bowers, Newport Beach, CA (US); Gregory F. Quinn, Fullerton, CA (US)

(73) Assignee: Enigma Science, LLC, Irvine, CA (US)

( * ) Notice: Subject to any disclaimer, the term of this patent is extended or adjusted under 35 U.S.C. 154(b) by 644 days.

This patent is subject to a terminal disclaimer.

(21) Appl. No.: 12/173,612

(22) Filed: Jul. 15, 2008

(65) Prior Publication Data

US 2009/0007704 A1    Jan. 8, 2009

Related U.S. Application Data

(63) Continuation-in-part of application No. 10/815,983, filed on Apr. 1, 2004, now Pat. No. 7,399,447.

(51) Int. Cl.
*G01N 1/14* (2006.01)

(52) U.S. Cl. .................... 422/68.1; 73/64.56; 73/863.01

(58) Field of Classification Search ................. 422/68.1; 73/64.56, 863, 863.01
See application file for complete search history.

(56) References Cited

U.S. PATENT DOCUMENTS

| | | | |
|---|---|---|---|
| 3,583,157 A | 6/1971 | Adams et al. | |
| 3,731,539 A | 5/1973 | Brittan et al. | |
| 3,838,719 A | 10/1974 | Lederer | |
| 3,841,156 A | 10/1974 | Wolfe | |
| 3,885,439 A | 5/1975 | Stone | |
| 3,921,178 A | 11/1975 | Weisgerber | |
| 4,527,968 A | 7/1985 | Ogawa | |
| 4,883,596 A | 11/1989 | Agui et al. | |
| 5,167,802 A | 12/1992 | Sandstrom et al. | |
| 5,299,141 A | 3/1994 | Hungerford et al. | |
| 5,319,986 A | 6/1994 | Padden et al. | |
| 5,341,834 A * | 8/1994 | Doherty et al. | 137/599.07 |
| 5,355,736 A | 10/1994 | Skogley | |
| 5,441,071 A | 8/1995 | Doherty et al. | |
| 6,178,831 B1 | 1/2001 | Dawson et al. | |
| 6,306,350 B1 | 10/2001 | Mereish et al. | |
| 6,564,655 B1 * | 5/2003 | Austen et al. | 73/863.02 |

FOREIGN PATENT DOCUMENTS

| | | |
|---|---|---|
| GB | 1367276 | 9/1974 |
| GB | 39 22 333 | 1/1991 |
| WO | WO 90/00250 | 1/1990 |
| WO | PCT/US2005/011005 | 6/2005 |

* cited by examiner

*Primary Examiner* — In Suk Bullock
*Assistant Examiner* — Paul Hyun
(74) *Attorney, Agent, or Firm* — Knobbe Martens Olson & Bear, LLP

(57) ABSTRACT

An active sampler for detecting contaminants in liquids comprises an inlet, an outlet and a sampling unit positioned such that the liquid flows along a path from the inlet, through the sampling unit, to the outlet. The sampling unit has a plurality of sampling chambers that are substantially fluidly sealed relative to one another, wherein one of the sampling chambers is selectively positioned in the flow path. The active sampler also comprises an actuator, which relatively moves the sampling unit and the inlet and outlet such that one sampling chamber is positioned out of the flow path while another of the sampling chambers is positioned in the flow path.

22 Claims, 7 Drawing Sheets

ACTIVE SAMPLER FOR DETECTING CONTAMINANTS IN LIQUIDS

CROSS-REFERENCE TO RELATED APPLICATIONS

This application is a continuation-in-part of U.S. application Ser. No. 10/815,983, filed Apr. 1, 2004, now U.S. Pat. No. 7,399,447 B2, the entire disclosure of which is hereby incorporated by reference herein and should be considered a part of this specification.

BACKGROUND OF THE INVENTION

1. Field of the Invention

The present invention is directed to sampling systems in general, and in particular, to an active sampler for detecting contaminants in liquids, such as water.

2. Description of the Related Art

Systems and apparatuses for sampling are common in the field of water monitoring, including determining the presence of contaminants in natural waterways (e.g., springs, rivers, and creeks), as well as in industrial and municipal discharges.

However, conventional sampling devices usually require the presence of a user at the site to manually take the liquid sample (e.g., in a test tube). The user then analyzes the samples by, for example, introducing chemicals into the sample to detect the presence of a contaminant.

Conventional sampling techniques typically involve taking discrete samples at widely spaced time intervals. Such discrete sampling makes it difficult to easily determine the accumulated concentration of a contaminant over the sampling period. Further, taking discrete samples is costly, particularly if samples need to be taken regularly (e.g., several times a month). The cost and inconvenience is further increased when the sampling of remote locations is desired.

Conventional active samplers, though able to continuously sample, generally require relatively large amounts of energy to pump the liquid through the sampler due to the large pressure differential through the system, thus making them unsuitable for use in remote locations without power. Additionally, these samplers can be bulky and unsuitable for deployment in shallow bodies of liquid or in piping infrastructure.

Accordingly, there is a need for an improved active sampling device for detecting contaminants in liquids.

SUMMARY OF THE INVENTION

In accordance with one aspect of the present invention, an active sampler for liquids is provided that comprises an inlet, an outlet, and a sampling unit positioned between the inlet and outlet, said sampling unit comprising a plurality of sampling chambers housing a sampling media therein. Each sampling chamber is selectively alignable with a flow path that extends from the inlet, through the sampling unit, to the outlet, the sampling chambers substantially fluidly sealed relative to one another. The flow path includes a first flow path section and a second flow path section, the first flow path section extending between the inlet and one end of the aligned sampling chamber, the second flow path section extending between the outlet and another end of the aligned sampling chamber. The sampling chamber interfaces with the first and second flow path sections via resilient sealing members so as to substantially seal the aligned sampling chamber in the flow path from the other sampling chambers. A pump is configured to pump liquid selectively through said flow path and the aligned sampling chamber. An actuator is configured to selectively align the flow path and one of the sampling chambers with each other and take the flow path and another of the sampling chambers out of alignment with each other. Each of the first and second flow path sections is configured to have minimal flow restrictions such that the pump can produce a flow rate of at least about 10 ml/min through the aligned sampling chamber while drawing generally on the order of about 250 mW of power, thereby increasing the operating time of the sampling unit for a given battery charge.

In accordance with one aspect of the present invention, an active sampler for liquids is provided that comprises an inlet, an outlet, and a sampling unit positioned between the inlet and outlet, said sampling unit comprising a plurality of sampling chambers housing a sampling media therein. Each sampling chamber is selectively alignable with a flow path that extends from the inlet, through the sampling unit, to the outlet, the sampling chambers substantially fluidly sealed relative to one another. The flow path includes a first flow path section and a second flow path section, the first flow path section extending between the inlet and one end of the aligned sampling chamber, the second flow path section extending between the outlet and another end of the aligned sampling chamber. The sampling chamber interfaces with the first and second flow path sections via resilient sealing members so as to substantially seal the aligned sampling chamber in the flow path from the other sampling chambers. A pump is configured to pump liquid selectively through said flow path and the aligned sampling chamber. An actuator is configured to rotate the sampling unit to move one of the sampling chambers into alignment with the flow path and to move another of the sampling chambers out of alignment with the flow path. Each of the first and second flow path sections is configured to have minimal flow restrictions.

In accordance with still another aspect of the present invention, an active sampler for liquids is provided that comprises an inlet, an outlet, and a rotatable sampling unit positioned between the inlet and outlet and removably attached to a housing of the active sampler, said sampling unit comprising a plurality of sampling chambers housing a sampling media therein. Each sampling chamber is selectively alignable with a flow path that extends from the inlet, through the sampling unit, to the outlet, the sampling chambers substantially fluidly sealed relative to one another. The flow path includes a first flow path section and a second flow path section, the first flow path section extending between the inlet and one end of the aligned sampling chamber, the second flow path section extending between the outlet and another end of the aligned sampling chamber. The sampling chamber interfaces with the first and second flow path sections via resilient sealing members so as to substantially seal the aligned sampling chamber in the flow path from the other sampling chambers. A pump is configured to pump liquid selectively through said flow path and the aligned sampling chamber. An actuator is configured to rotate the sampling unit to move one of the sampling chambers into alignment with the flow path and to move another of the sampling chambers out of alignment with the flow path. Each of the first and second flow path sections is configured to have minimal flow restrictions.

DETAILED DESCRIPTION OF THE PREFERRED EMBODIMENT

Figure 1:
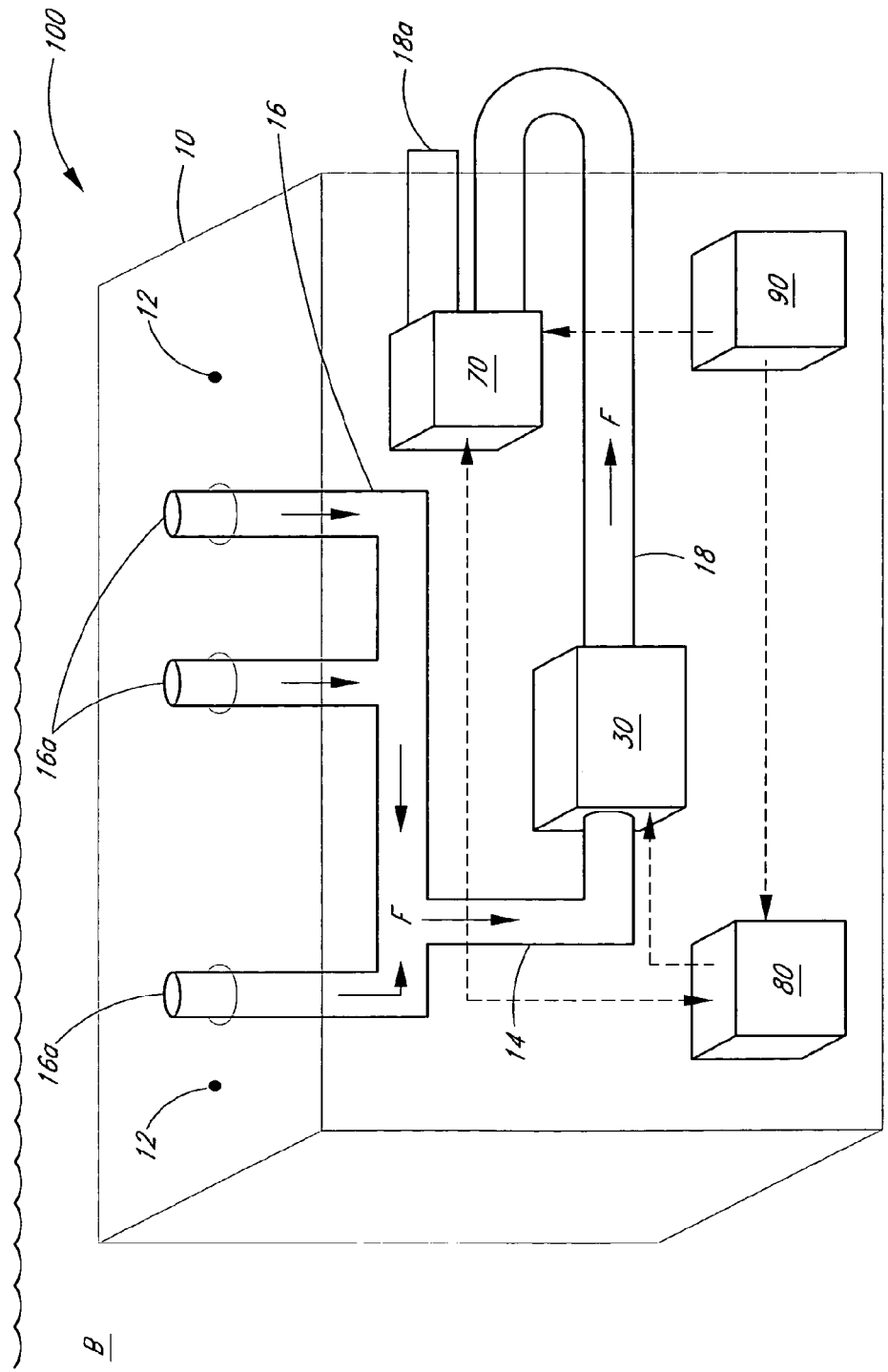
FIG. 1 is a schematic view of a liquid sampler.

FIG. 1 schematically illustrates one embodiment of an active liquid sampler 100 disposed in a body of liquid B. The liquid sampler 100 comprises an inlet tube 14 connected to a sampling unit 30. The inlet tube 14 receives a liquid flow F through at least one inlet port 16a, and delivers it to the sampling unit 30. In the illustrated embodiment, the inlet tube 14 is connected to an inlet manifold 16, which provides multiple inlet ports 16a into the liquid sampler 100. However, in other embodiments, the inlet tube 14 can extend from the inlet port 16a to the sampling unit 30, without the manifold 16 present. The liquid flow F passes from the sampling unit 30 to an outlet tube 18. The inlet and outlet tubes 14, 18 can be any suitable conduit for carrying the liquid flow F and have one of a variety of cross-sectional shapes, such as circular, square and oval. The liquid flow F through the sampler 100 is generated by a pump 70 connected between the outlet tube 18 and a pump discharge pipe 18a. The pump 70 passes liquid through the inlet tube 14, sampling unit 30 and outlet tube 18. The pump 70 then discharges the fluid back to the body of liquid B via an outlet port on the end of the pump discharge pipe 18a. The liquid sampler 100 also comprises at least one battery 90, which provides power to the pump 70, as well as to a system controller 80 that controls the operation of the pump 70 and the sampling unit 30.

As shown in FIG. 1, the components of the liquid sampler 100 are preferably disposed in a housing 10. The housing 10 includes at least two electrical contacts 12 in proximity to the inlet ports 16a. The housing 10 preferably maintains the liquid sampler 100 in a substantially sealed environment to, among other things, prevent the short-circuiting of the battery 90 or system controller 80. The electrical contacts 12 are preferably exposed such that immersion of the housing 10 in the body of liquid B lowers the electrical resistance between the contacts 12. The system controller 80 senses such low resistance and starts the pump 70 in response to sensing such low resistance. Likewise, extraction of the housing 10 from the body of liquid B would increase the electrical resistance between the contacts 12. In response to sensing such high increased resistance, the system controller 80 would stop the pump 70.

Figure 2:
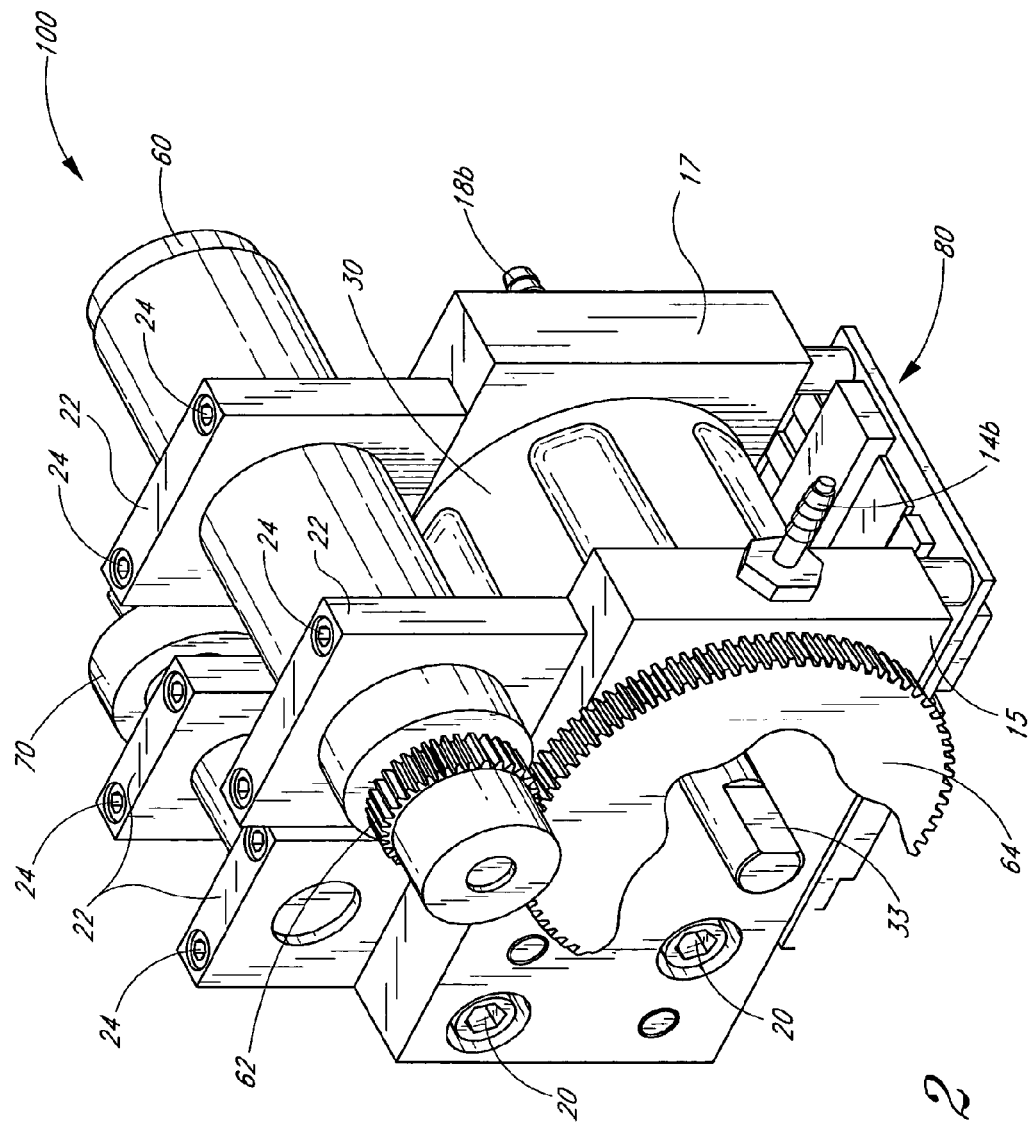
FIG. 2 is a top, front and side perspective view of one embodiment of a liquid sampler.
Figure 3:
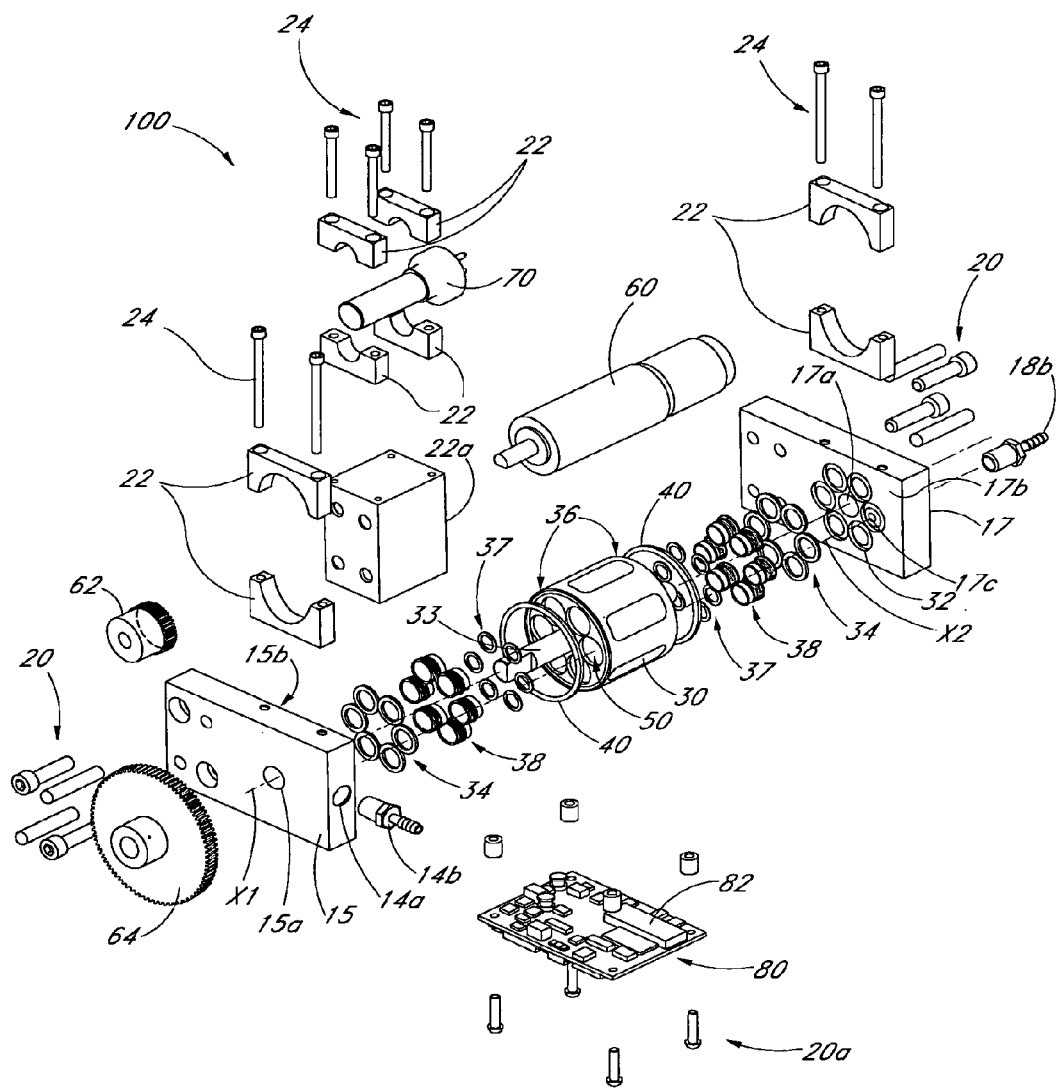
FIG. 3 is an exploded view of the liquid sampler shown in FIG. 2.

FIGS. 2 and 3 illustrate further details of the active liquid sampler 100. In the illustrated embodiment, an inlet fitting 14b connects to an inlet wall 15 at the inlet port 14a (shown in FIG. 3). The liquid sampler 100 also has an outlet fitting 18b connected to an outlet wall 17 at an outlet port (not shown) of the pump discharge pipe 18a (see FIG. 1). As shown in FIG. 3, both the inlet wall 15 and outlet wall 17 each have an opening 15a, 17a therethrough configured to receive a shaft 33 connected to the sampling unit 30, where the shaft 33 preferably extends longitudinally through a central axis X1 of the sampling unit 30.

As best shown in FIG. 3, each of the inlet and outlet walls 15, 17 comprises an inner surface 15b, 17b having grooves 32 disposed about the opening 15a, 17a that receives the shaft 33 of the sampling unit 30. Additionally, the inner surfaces 15b, 17b of the walls 15, 17 are preferably a mirror image of each other. In the illustrated embodiment, a plurality of circular grooves 32 is shown. However, the grooves 32 can have other shapes, such as square and oval. Each groove 32 preferably receives an O-ring 34 or other resilient sealing member therein. One of the grooves 32 surrounds a flow port 17c in the outlet wall 17, which preferably communicates with the outlet fitting 18b through a flow path (not shown) in the outlet wall 17. Similarly, one of the grooves 32 on the inner surface 15b surrounds a flow port (not shown) in the inlet wall 15 that communicates with the inlet port 14a and inlet fitting 14b through a flow path (not shown) in the inlet wall 15. Preferably, both flow ports are aligned with each other about an axis X2 extending between the walls 15, 17.

The sampling unit 30 shown in FIG. 3 comprises sampling chambers 50 extending between two ends 36 of the unit 30, each chamber 50 housing a sampling medium (not shown). In a preferred embodiment, the sampling medium is Ambersorb®. However, the sampling medium can comprise other suitable sorbent materials. Each sampling chamber 50 preferably contains an amount of sorbent material suitable for sampling contaminants or pollutants in a liquid. In a preferred embodiment, each sampling chamber 50 contains less than about 1000 mg of sorbent material. In another preferred embodiment, each sampling chamber 50 contains between approximately 100 and 2000 mg of sorbent material. Another embodiment contains approximately 200 mg of sorbent material.

In the embodiment illustrated in FIG. 3, the sampling unit 30 comprises a carousel cartridge with six sampling chambers 50. However, one of ordinary skill in the art will recognize that the sampling unit 30 can have a number of shapes, as well as have more or less sampling chambers 50. The sampling medium is preferably held in place in the chambers 50 by a screen 37 disposed at each end 36. In a preferred embodiment, the screen 37 is approximately a 100-micron stainless steel screen. In another preferred embodiment the screen 37 is between approximately 10 and 200 microns. In yet another embodiment, the screen 37 is approximately a 20 micron screen. However, other suitable screen sizes or materials can be used. In the illustrated embodiment, a screen insert 38 is disposed over each screen 37 to hold the screen 37 substantially in place against the sampling medium. In one preferred embodiment, the screen insert 38 has a threaded surface (not shown) for engaging a corresponding threaded portion (not shown) of each end 36 of the sampling chamber 50. In other embodiments, the screen insert 38 is integral with the screen 37. Additionally, a seal 40, such as an O-ring, is disposed about the periphery of each end 36 of the carousel cartridge 30. The seal 40 substantially prevents liquid from leaking out of the carousel cartridge 30.

When the liquid sampler 100 shown in FIG. 3 is assembled with the O-rings 34, the sampling chambers 50 are maintained substantially fluidly isolated from each other. Accordingly, fluid in one of the sampling chambers 50 is substantially prevented from entering another of the chambers 50. Also, as discussed above, the flow ports through the walls 15, 17 are generally aligned with each other about axis X2. The carousel cartridge 30 is disposed such that the axis X2 is aligned with and extends longitudinally through one of the chambers 50. In the disclosed embodiment, fluid flow from the inlet fitting 14b to the outlet fitting 18b passes through only the sampling chamber 50 that is aligned with the axis X2. Thus, only one of the chambers 50 of the carousel cartridge 30 will receive fluid at any one time.

The carousel cartridge 30 includes a shaft 33 which rotatably mounts the carousel cartridge 30 on openings 15a, 17a in the inlet and outlet walls 15, 17. The shaft 33 permits the carousel cartridge 30 to rotate about the axis X1. The walls 15, 17 are preferably maintained in fixed relation to each other via at least one fastener 20. In the illustrated embodiment, the at least one fastener 20 includes a plurality of bolts. However, other fasteners can be used, such as screws, brackets, adhesives and bands.

As shown in FIGS. 2 and 3, the liquid sampler 100 includes an actuator 60, such as an electric motor, which drives the carousel cartridge 30 to rotate about the axis X1. Preferably, the actuator 60 receives power from, for example, a battery (not shown). The actuator 60 and the pump 70 are preferably removably connected to the inlet and outlet walls 15, 17. In the illustrated embodiment, the actuator 60 and the pump 70 are connected to the walls 15, 17 via at least one bracket 22 and at least one fastener 24; the bracket 22 supporting the pump 70 rests on a support 22a.

As best shown in FIGS. 2 and 3, in one embodiment, the actuator 60 is connected to a drive gear 62, which drives a driven gear 64 (see FIG. 3) on the end of the shaft 33. Accordingly, the actuator 60 rotates the carousel cartridge 30 via the gears 62, 64. However, the actuator 60 can drive the shaft 33 via other means, such as belts, chains or straps.

Figure 4:
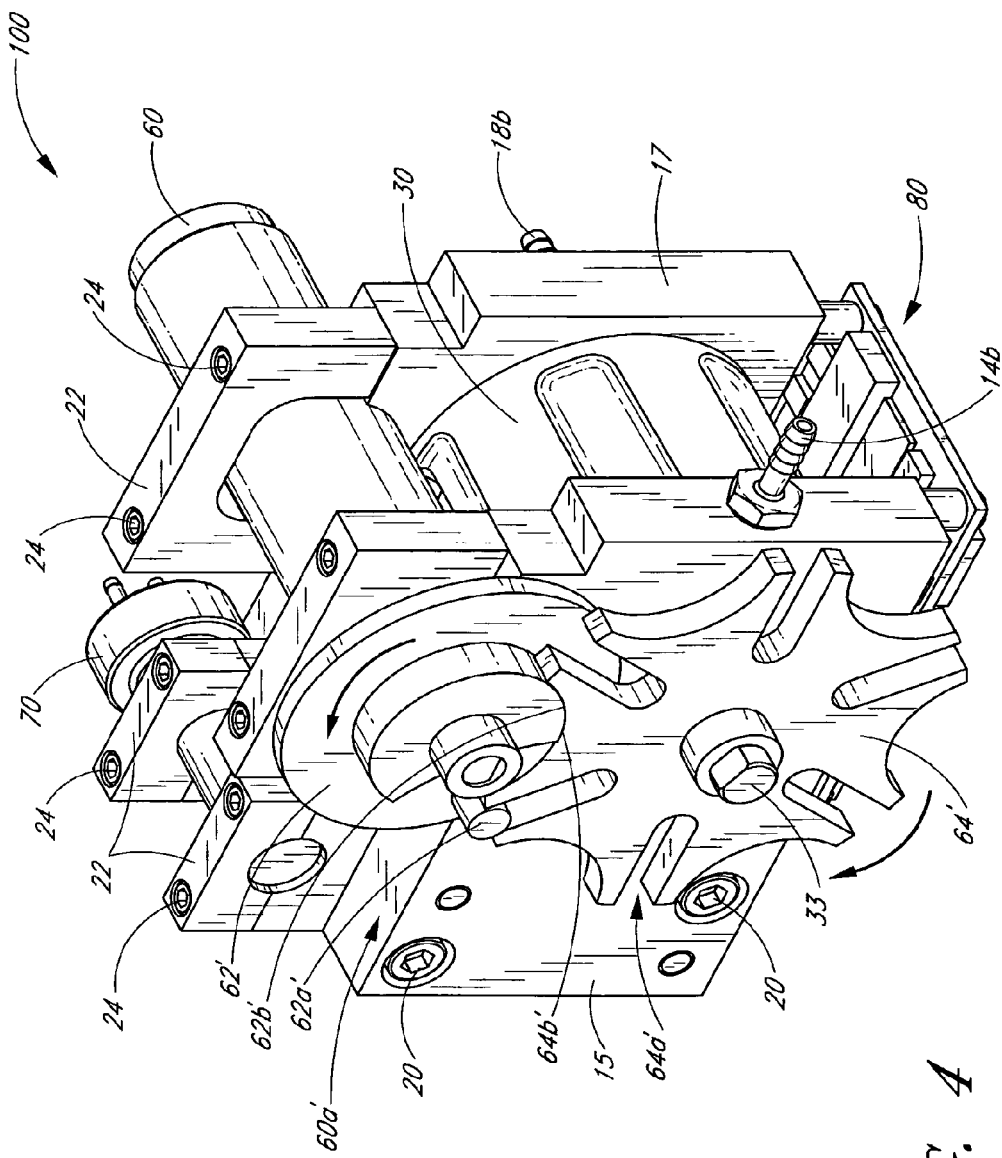
FIG. 4 is a top, front and side perspective view of another embodiment of a liquid sampler.

In another embodiment, as shown in FIG. 4, the actuator 60 rotates the carousel cartridge 30 via a Geneva mechanism 60a'. Preferably, the Geneva mechanism 60a' comprises a first rotatable member 62' engageable with a second rotatable member 64', wherein the rotatable members 62', 64' rotate in opposite directions. The first rotatable member 62' connects to the actuator 60 and includes a protruding member 62a', such as a pin, disposed at the periphery of the first rotatable member 62'. The second rotatable member 64' has a plurality of longitudinal slots 64a' and connects to the end of the shaft 33 that extends through the opening 15a of the inlet wall 15. Each slot 64a' is configured to slidingly receive the protruding member 62a' during rotation of the first rotatable member 62'. The slots 64a' receive a force from the protruding member 62a' to rotate the second rotatable member 64'. Rotation of the second rotatable member 64' rotates the carousel cartridge 30 connected thereto. The first rotatable member 62' also preferably includes an edge 62b' that engages an edge 64b' of the second rotatable member 64' to prevent the rotation of the second rotatable member 64' when the protruding member 62a' is outside the slots 64a'.

As the actuator 60 rotates the first rotatable member 62', the protruding member 62a' slidingly moves into one of the slots 64a'. As the first rotatable member 62' continues to rotate, the protruding member 62a' transfers a force to the slot 64a', causing the second rotatable member 64' to rotate until the protruding member 62a' exits the slot 64a'. Preferably, rotation of the second rotatable member 64' rotates the carousel cartridge 30 to place a different sampling chamber 50 (see FIG. 5) in communication with the flow path of the liquid sampler 100. While the protruding member 62a' is outside of the slot 64a', the edges 62b', 64b' of the first and second rotatable members 62', 64', respectively, engage each other to prevent the rotation of the second rotatable member 64'. Similarly, the edges 62b', 64b' do not engage each other while the protruding member 62a' transfers a force to the slot 64a' to rotate the second rotatable member 64'. The Geneva mechanism 60a' provides repeatably accurate alignment of the sampling chamber 50 (see FIG. 5) with the flow path of the sampler 100. Additionally, the geneva mechanism 60a' does not require use of feedback control to ensure correct alignment of the sampling chamber 50 with the flow path.

Figure 5:
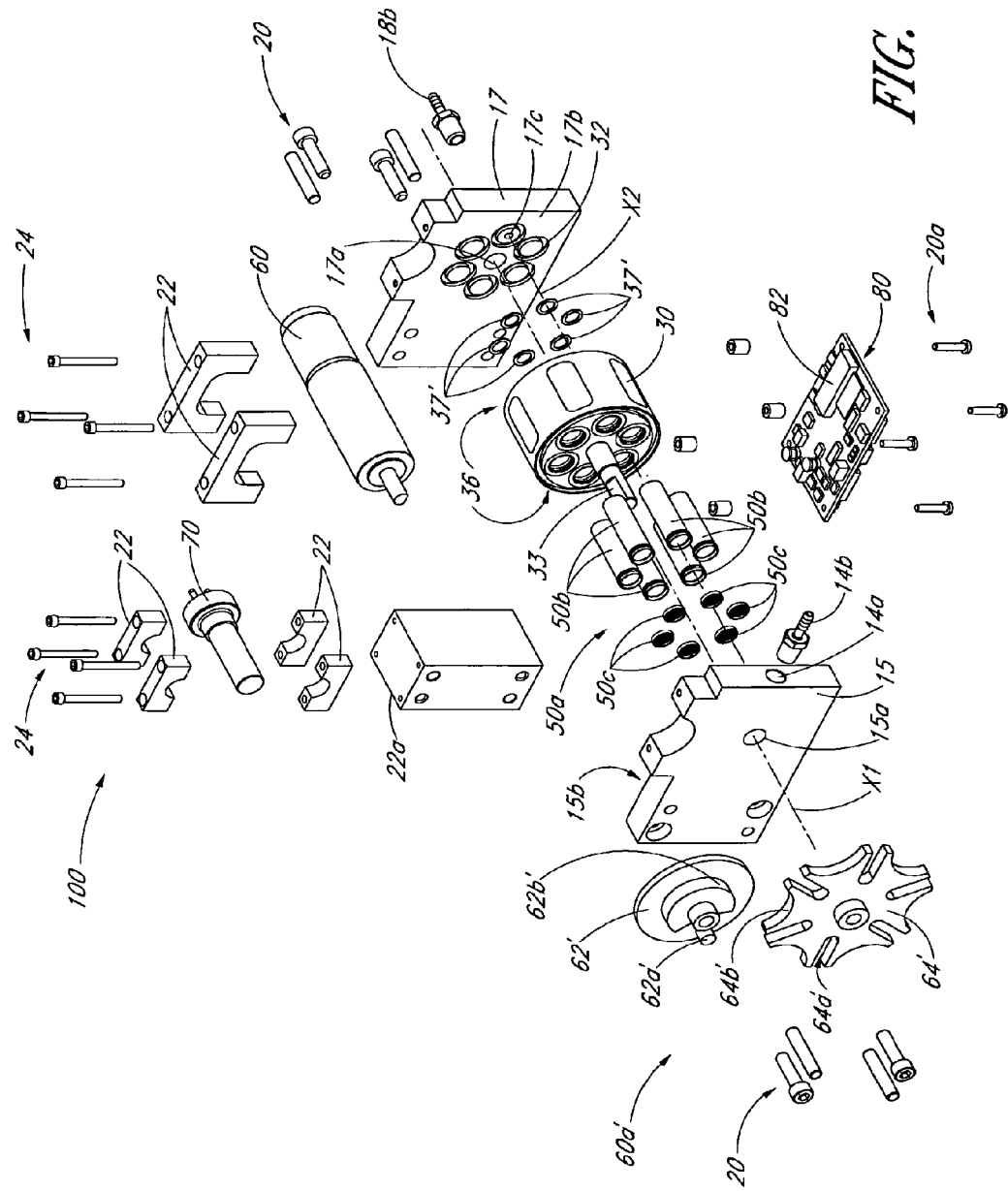
FIG. 5 is an exploded view of the liquid sampler shown in FIG. 4.

As illustrated in FIG. 5, in one preferred embodiment, the liquid sampler 100 comprises a plurality of sorbent cartridges 50a, preferably one for every sampling chamber 50, that house the sorbent material therein. The sorbent cartridges 50a preferably comprise a tube portion 50b and a cap portion 50c. The sorbent cartridges 50a are preferably permeable to allow a liquid passing through the sampling chamber 50 to contact the sorbent material. For example, the sorbent cartridges 50a can have a meshed surface. Preferably, the cartridges 50a securely and removably fit in the sampling chambers 50. For example, the cap portion 50c can connect with one end 36 of the sampling chamber 50 in a snap-fit manner once the cartridge 50a is inserted in the sampling chamber 50. Additionally, a screen 37' is attached to the bottom of the tube portion 50b of each sorbent cartridge 50a. For example, the screen 37' can be molded to the tube portion 50b. In another embodiment, the screen 37' is attached to the end 36 of each sampling chamber 50 opposite the end 36 through which the sorbent cartridge 50a is inserted. The sorbent cartridges 50a may be loaded or unloaded similar to bullets in a revolver, thereby providing for easy deployment of sorbent material in the sampling chambers 50, and for easy removal of sorbent material from said chambers 50.

As mentioned, the pump 70 provides liquid flow F through the flow path of the sampler 100. Preferably, the pump 70 is adapted to provide a relatively high volumetric flow through the sampler 100 while requiring a low power input to do so. The preferred pump 70 is capable of pumping at least about 10 ml/min of liquid while drawing no more than about 250 mW from the battery 90 when the liquid flows through the pump without a pressure drop. In one embodiment the pump 70 can pump at least about 10 ml/min of liquid while drawing a current of no more than 30 mA from the battery 90 when the liquid flows through the pump without a pressure drop. In another embodiment, the pump 70 can pump liquid while drawing a current of no more than about 40 mA at a voltage of approximately 6 Vdc. Another preferred pump 70 is capable of pumping at least about 50 ml/min of liquid while drawing a current of no more than about 50 mA with a drive voltage of approximately 5 Vdc when the liquid flows without a pressure drop.

Figure 6:
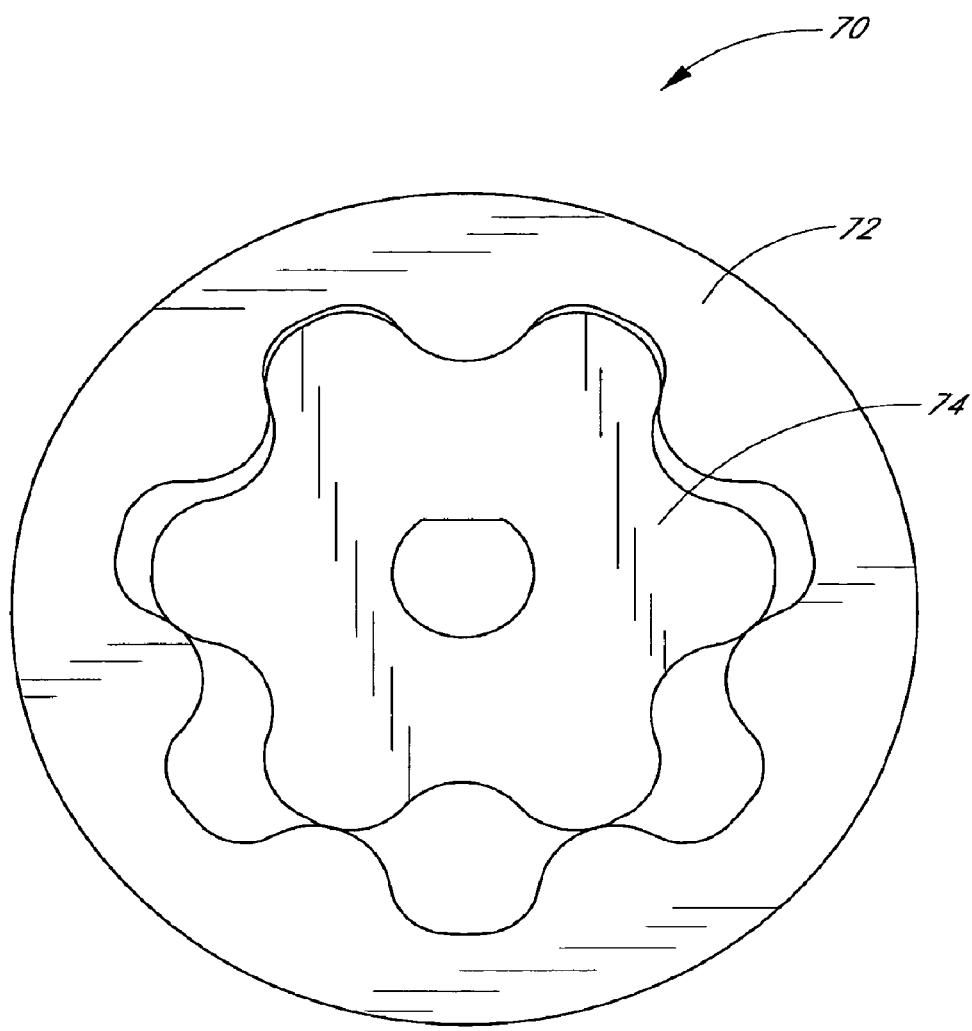
FIG. 6 is a cross-sectional view of a pump used in conjunction with one embodiment of a liquid sampler.

In one embodiment, shown in FIG. 6, the pump 70 comprises a pair of rotatable members 72, 74, which pump liquid by rotating at different speeds in the same direction. One example of such a pump 70 is a gear rotor or "gerotor" pump, wherein the rotatable members 72, 74 are gears which engage each other. Gerotor pumps are available from a variety of suppliers, such as Enigma Science of Irvine, Calif., Mesoscopic Devices of Broomfield, Colo. and Diener Precision Pumps of Switzerland. However, other suitable pumps can be used that meet the flow and current requirements discussed above.

In one embodiment, shown in FIGS. 2 and 3, the pump 70 is disposed downstream of the carousel cartridge 30. Accordingly, the pump 70 draws liquid from the body of liquid B, through the inlet fitting 14b, through the sampling chamber 50 that is in the fluid flow path, and through the outlet fitting 18b, before the liquid flow F enters the pump 70. A conduit preferably connects the outlet fitting 18b with the inlet port (not shown) of the pump 70. Additionally, the pump discharge pipe 18a (see FIG. 1) preferably connects to the outlet port (not shown) of the pump 70, through which the liquid flow F is returned to the body of liquid B. In another embodiment (not shown), the pump 70 can be disposed upstream of the inlet fitting 14b and drive liquid through the carousel cartridge 30.

The pump 70 is preferably small in size, requires a low power input, has a low audible noise, and is chemically inert. The pump 70 can preferably operate in a reverse mode to backflush liquid flow F through the liquid sampler 100, as described further below. Additionally, the pump 70 is preferably self-priming and can operate with particles less than about 50 microns in size that may be present in the liquid flow F.

The fittings 14, 18 and sampling unit 30, shown in FIG. 3, are preferably made of corrosion-resistant materials. For example, they can be made of stainless steel. The actuator 60 and pump 70 are preferably also made of corrosion-resistant materials. The liquid sampler 100 is also preferably made of chemically inert materials that will not react with any pollutants in the body of liquid B being sampled, or add contaminants into the liquid (i.e., self-contamination).

The system controller 80 of the active liquid sampler 100 illustrated in FIG. 3 includes a microprocessor 82 that, among other things, controls the operation of the actuator 60 and the pump 70. In the illustrated embodiment, the system controller 80 is connected to the liquid sampler 100 via fasteners 20*a*, such as bolts. However, other fasteners can be used, such as screws, brackets, adhesives and bands. The system controller 80 preferably comprises a power management module, a real-time clock, a user interface, at least one environmental sensor, firmware and adequate non-volatile memory. The memory is preferably Flash memory. The controller 80 preferably draws the lowest possible current. In a preferred embodiment, the controller 80 draws less than approximately 5 mA at about 3 Vdc input with all of its circuitry active. In another preferred embodiment, the controller 80 draws less than about 3 mA during sample collection, not including the current drawn by the pump 70. In yet another preferred embodiment, the controller 80 draws a current in the μA range when in a sleep mode.

The microprocessor 82 is the central processing unit of the liquid sampler 100 and preferably controls and manages all aspects and functions of the sampler 100. For example, the microprocessor 82 controls and manages the user interface, data acquisition, data processing and storage, sampler 100 activation, and long term monitoring of sampler 100 state of health. Preferably, the microprocessor 82 selectively signals the actuator 60 to rotate the carousel cartridge 30 so that the sampling chamber 50 communicating with the flow path is taken out of the flow path and a different sampling chamber 50 is brought into communication with the flow path. Additionally, the microprocessor 82 monitors the current draw of the pump 70. Preferably, the microprocessor 82 signals the pump 70 to operate in a backflush mode when the microprocessor 82 receives a current draw signal from the pump 70 that is higher than a preset value. Upon receiving the signal to operate in backflush mode, the pump 70 operates in reverse, causing fluid to pass from the outlet tube 18, through the sampling chamber 50, through the inlet tube 14, and back to the body of liquid B. In one embodiment, the microprocessor 82 signals the pump 70 to operate in backflush mode when it receives a current draw signal from the pump 70, while in sampling mode, that is greater than about 80 mA. The microprocessor 82 also logs when it initiates operation of the pump 70 and collects an operation history of the liquid sampler 100.

In a preferred embodiment, the microprocessor 82 meets the power or energy constraints (i.e., power required times operation time) of the sampler 100. The power consumption of the liquid sampler 100 is preferably less than about 400 mW when fully operational. In one embodiment, the power consumption of the liquid sampler 100 can be less than about 55 mA. One such microprocessor 82 is model number PIC18LF8720 by Microchip, Inc. In one embodiment, the microprocessor 82 preferably generates a pulse-width-modulated (PWM) signal under software control to operate the pump 70 and to rotate the carousel cartridge 30 via the actuator 60. PWM drive signals advantageously result in a lower current draw since the "on" duty cycle is less than 100%. An H-bridge controller in the system controller 80 obtains the PWM input signal from the microprocessor 82 and the DC voltage required to drive the pump 70 and carousel cartridge 30. The H-bridge imposes the PWM signal onto a steady state drive voltage, resulting in a replicated PWM signal that is at the voltage level of the pump 70 drive voltage. Preferably, the frequency of the duty cycle is optimized so that maximum operation is obtained at the lowest current draw. In a preferred embodiment, the pump 70 requires a drive voltage of 4.5 volts, and the replicated PWM signal is a square wave alternating between 0 volts and 4.5 volts at a frequency of approximately 19 kHz with approximately a 78% duty cycle. Additionally, the H-bridge controller preferably drives both bi-directional DC Brush and single winding stator motors. The bi-directional drive capability can be used to operate the pump 70 in a backflush mode to reverse the direction of liquid flow F through the liquid sampler 100 if the sampler 100 starts to become clogged, as detected by an increase in the current drawn by the pump 70.

The user interface of the system controller 80 allows a user to interface with the liquid sampler 100 to determine the status and "state-of-health" of the sampler 100. For example, a user can upload a new sample collection schedule or download archived data from the internal log. In a preferred embodiment, the user interface comprises a Universal Serial Bus (USB) style port. One suitable USB port is model number CY7C63723 by Cypress Semiconductor.

In one embodiment, the system controller 80 comprises a temperature sensor, which monitors the temperature of the controller 80. The controller 80 preferably archives the temperature every time an event is logged, in order to create a temperature history. Preferably, the controller 80 archives the temperature reading, along with the date and current reading, during at least the following events: when the sensor contacts 12 indicate a liquid is present; when the sensor contacts 12 indicate a liquid is absent; when the sampler 100 operates in backflush mode; detection of mechanical or electrical faults in the system or other system failure; sensing of current above a set value (e.g., because the pump 70 is clogged); inability to backflush the sampler 100 when in backflush mode; lack of battery power; and rotation of the sampling unit 30. In a preferred embodiment, at least the following parameters will be logged during any one of the events noted above: temperature, battery voltage, pump drive voltage, pump current, time, date, and carousel cartridge 30 number. Advantageously, the temperature history provides environmental data over the course of the deployment of the liquid sampler 100, or in the event of a system failure. In other embodiments, the system controller 80 can have environmental sensors to detect, for example, pH, conductivity, turbidity, or a desired chemical signature in the body of liquid being sampled. In some preferred embodiments, one or both of the temperature and environmental sensors can be used to trigger the operation of the liquid sampler 100, as described below.

Figure 7:
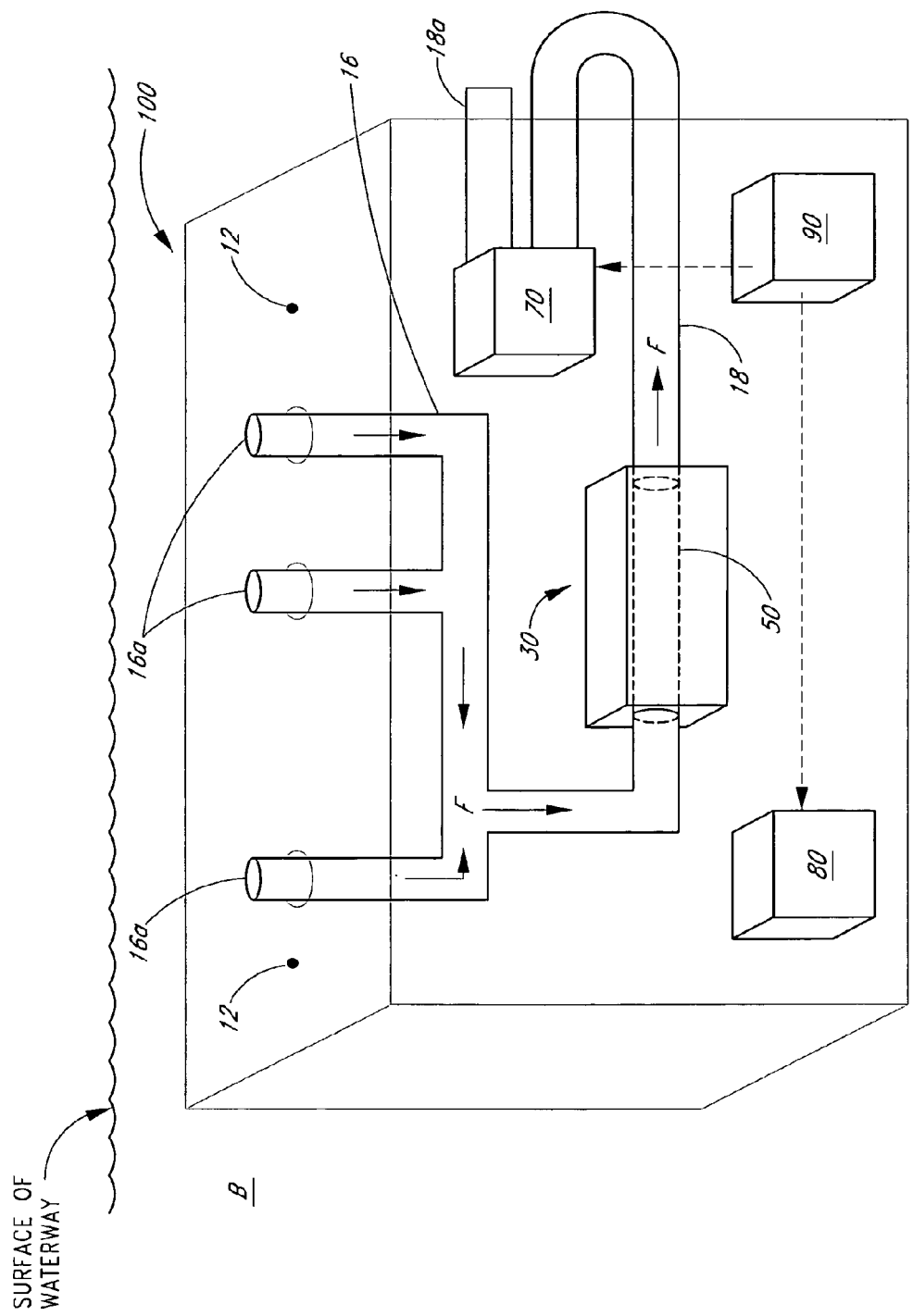
FIG. 7 is a schematic view of flow through a liquid sampler according to one embodiment.

FIG. 7 illustrates the operation of one embodiment of the liquid sampler 100. In the illustrated embodiment, liquid from a body of liquid B flows into the inlet manifold 16 through the inlet ports 16*a* and subsequently enters the sampling unit 30. The liquid flow F passes through one of the chambers 50 in the sampling unit 30, which has been selectively placed in communication with the flow path of the liquid sampler 100. The liquid flow F then passes through the outlet tube 18 and the pump 70 before being discharged back to the body of liquid B. At least one battery 90 provides power to the system controller 80, actuator (not shown) and pump 70. Preferably, the battery 90 is capable of providing a voltage of approximately 3.6 volts. In one preferred embodiment, the battery 90 is a lithium battery. In another preferred embodiment, the battery 90 is an alkaline battery.

In one embodiment, the liquid sampler 100 can operate continuously upon deployment in a body of liquid. That is, as soon as the sampler 100 is submerged into a body of liquid, the system controller 80 senses the lowered resistance between the electrical contacts 12 and starts the operation of the pump 70. The pump 70 therefore runs continuously for the duration of the sampling period. The system controller 80 also indexes the carousel 30 to place one of the sampling chambers 50 in communication with the flow path of the sampler 100. In a preferred embodiment, the system controller 80 indexes the carousel 30 every two weeks to place a different sampling chamber 50 in communication with the flow path. In the embodiment shown in FIG. 3, where the carousel 30 has six sampling chambers 50, the total sampling period is approximately ten weeks, with one chamber 50 preferably used as a control chamber and thus not placed in communication with the flow path. However, one of ordinary skill in the art will recognize that the sampling period per chamber 50 and the total sampling period can be varied, as desired by the user. For example, in another embodiment, the user can program the liquid sampler 100 to index the carousel 30 every week.

In another embodiment, the liquid sampler 100 can be in sleep mode upon deployment in a body of liquid and initiate operation via the triggering of a sensor. For example, the liquid sampler 100 can initiate operation upon detection of an acid in the body of liquid by the environmental sensor (e.g., a pH sensor). The sensor would preferably signal the controller 80 of the triggering event, and the controller 80 would initiate operation of the pump 70 and index the carousel cartridge 30 as described above. Optionally, the system controller 80 can communicate with a user upon the triggering of the sensor via, for example, phone, page or the internet.

The liquid sampler 100 described herein advantageously provides a compact unit that actively samples liquid over a period of time without the need for a user to manually take said samples. In one embodiment, the liquid sampler 100 has a total volume of approximately 40 in$^3$. In another embodiment, the liquid sampler 100 has a total volume between approximately 30 and 100 in$^3$. Accordingly, the liquid sampler 100 can advantageously operate in shallow bodies of liquid and be incorporated into the plumbing infrastructure of a building to monitor liquid quality. The compact size of the liquid sampler 100 also advantageously reduces manufacturing costs and makes the sampler 100 easier to carry or transport.

The liquid sampler 100 can advantageously be used in various applications to monitor liquid quality in bodies of liquid. In one embodiment, the liquid sampler 100 can be used to monitor the presence of chemicals in a body of liquid. In another embodiment, the liquid sampler 100 can be used to monitor bacteria. Accordingly, the liquid sampler 100 can detect a variety of pollutants dumped into a body of liquid, such as a stream, a river, or a piping system.

The liquid sampler 100 can advantageously be disposed in a body of liquid at a remote location and left in the body of liquid for an extended period of time, after which a user can return to extract the sampler 100 from the body of liquid. The user can then remove the sampling unit 30 from the sampler 100 and place it on an extraction jig (not shown). The extraction jig preferably holds the sampling unit 30 and directs an extraction solvent through one end of each sampling chamber 50 and into a corresponding container (e.g., a vial) disposed at the opposite end of the chamber 50. Accordingly, the extraction jig advantageously allows a user to extract all of the sampling chambers 50 of the sampling unit 30 at the same time using the same process. Additionally, the sampling unit 30 advantageously provides the sampler 100 with a single unit that can easily be handled by a user, instead of multiple individual cartridge tubes.

Another advantage of the liquid sampler 100 is that it can operate for a prolonged period of time without requiring a significant power input. The liquid sampler 100 is capable of operating for the entire sample period using one battery pack 90. In a preferred embodiment, the liquid sampler 100 requires a voltage of approximately 3.6 volts to operate for the entire sample period. In another preferred embodiment, the liquid sampler 100 requires approximately 3 volts to operate for the entire sample period. In yet another preferred embodiment, the liquid sampler 100 requires approximately 1.8 volts to operate for the entire sample period. Moreover, the pump 70 preferably draws at least about 10 ml/min through the liquid sampler 100 while drawing no more than about 250 mW of power from the battery pack 90. In one embodiment, the pump 70 draws at least about 10 ml/min through the liquid sample 100 while drawings no more than about 30 mA from the battery pack 90.

Still another advantage of the liquid sampler 100 is that it has a minimal pressure drop. Unlike conventional designs, which use valves to fluidly isolate sampling chambers, the liquid sampler 100 is a valve-less system. Valves are undesirable because they increase the pressure drop through the sampling system, resulting in a loss of volumetric flow through the system, as well as an increased power input required by the pump. The sampling unit 30 operates at a minimal pressure drop by using resilient sealing members, such as O-rings, to isolate each of the sampling chambers 50 and pump liquid through the sampling unit 30 and inlet and outlet tubes 14, 16. In a preferred embodiment, the pressure drop through the liquid sampler is no more than about 40 inches of $H_2O$. Accordingly, the liquid sampler 100 is can operate at the conditions described above without requiring substantial power input.

For the purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. All of these aspects are intended to be within the scope of the invention herein disclosed.

These and other aspects of the present invention will become readily apparent to those skilled in the art from the appended claims and from the proceeding detailed description of the preferred embodiments having reference to the attached figures, the invention not being limited to any particular preferred embodiments disclosed.

What is claimed is:

1. An active sampler for liquids, comprising:
   an inlet;
   an outlet;
   a sampling unit positioned between said inlet and outlet, said sampling unit comprising a plurality of sampling chambers housing a sampling media therein, each sampling chamber being selectively alignable with a flow path that extends from the inlet, through the sampling unit, to the outlet, the sampling chambers substantially fluidly sealed relative to one another, the flow path including a first flow path section and a second flow path section, the first flow path section extending between the inlet and one end of the aligned sampling chamber, the second flow path section extending between the outlet and another end of the aligned sampling chamber, the sampling chamber interfacing with the first and second flow path sections via resilient sealing members so as to substantially seal the aligned sampling chamber in the flow path from the other sampling chambers;

a pump configured to pump liquid selectively through said flow path and the aligned sampling chamber; and an actuator configured to selectively align the flow path and one of the sampling chambers with each other and take the flow path and another of the sampling chambers out of alignment with each other, wherein each of the first and second flow path sections is configured to have minimal flow restrictions such that the pump can produce a flow rate of at least about 10 ml/min through the aligned sampling chamber while drawing generally on the order of about 250 mW of power, thereby increasing the operating time of the sampling unit for a given battery charge.

2. The active sampler of claim 1, wherein the inlet comprises a manifold having multiple inlet ports.

3. The active sampler of claim 1, wherein the sampling unit is a cartridge detachable from the active sampler.

4. The active sampler of claim 3, wherein the cartridge is a revolving carousel configured to move relative to the inlet and outlet to align the flow path with one of the sampling chambers, while taking another sampling chamber out of alignment with the flow path.

5. The active sampler of claim 1, wherein the plurality of sampling chambers are substantially fluidly sealed relative to one another by O-rings disposed at the ends of each chamber.

6. The active sampler of claim 1, wherein the sampling media is a sorbent material.

7. The active sampler of claim 5, wherein the sorbent material is an adsorbent material.

8. The active sampler of claim 1, wherein the actuator relatively moves said sampling unit and said path using a Geneva mechanism.

9. The active sampler of claim 1, wherein the pump comprises a pair of rotatable members that pump said liquid flow by rotating at different rates in the same direction.

10. An active sampler for liquids, comprising:
an inlet;
an outlet;
a sampling unit positioned between said inlet and outlet, said sampling unit comprising a plurality of sampling chambers housing a sampling media therein, each sampling chamber being selectively alignable with a flow path that extends from the inlet, through the sampling unit, to the outlet, the sampling chambers substantially fluidly sealed relative to one another, the flow path including a first flow path section and a second flow path section, the first flow path section extending between the inlet and one end of the aligned sampling chamber, the second flow path section extending between the outlet and another end of the aligned sampling chamber, the sampling chamber interfacing with the first and second flow path sections via resilient sealing members so as to substantially seal the aligned sampling chamber in the flow path from the other sampling chambers;
a pump configured to pump liquid selectively through said flow path and the aligned sampling chamber; and
an actuator configured to rotate the sampling unit to move one of the sampling chambers into alignment with the flow path and to move another of the sampling chambers out of alignment with the flow path.

11. The system of claim 10, wherein the pump can produce a flow rate of at least about 10 ml/min through the aligned sampling chamber while drawing generally on the order of about 250 mW of power, thereby increasing the operating time of the sampling unit for a given battery charge.

12. The active sampler of claim 10, wherein the inlet comprises a manifold having multiple inlet ports.

13. The active sampler of claim 10, wherein the sampling unit is a cartridge detachable from the active sampler.

14. The active sampler of claim 10, wherein the sampling media is a sorbent material.

15. The active sampler of claim 14, wherein the sorbent material is an adsorbent material.

16. The active sampler of claim 10, wherein the actuator relatively moves said sampling unit and said path using a Geneva mechanism.

17. The active sampler of claim 10, wherein the pump comprises a pair of rotatable members that pump said liquid flow by rotating at different rates in the same direction.

18. An active sampler for liquids, comprising:
an inlet;
an outlet;
a rotatable sampling unit positioned between said inlet and outlet and removably attached to a housing of the active sampler, said sampling unit comprising a plurality of sampling chambers housing a sampling media therein, each sampling chamber being selectively alignable with a flow path that extends from the inlet, through the sampling unit, to the outlet, the sampling chambers substantially fluidly sealed relative to one another, the flow path including a first flow path section and a second flow path section, the first flow path section extending between the inlet and one end of the aligned sampling chamber, the second flow path section extending between the outlet and another end of the aligned sampling chamber, the sampling chamber interfacing with the first and second flow path sections via resilient sealing members so as to substantially seal the aligned sampling chamber in the flow path from the other sampling chambers;
a pump configured to pump liquid selectively through said flow path and the aligned sampling chamber; and
an actuator configured to rotate the sampling unit to move one of the sampling chambers into alignment with the flow path and to move another of the sampling chambers out of alignment with the flow path.

19. The system of claim 18, wherein the pump can produce a flow rate of at least about 10 ml/min through the aligned sampling chamber while drawing generally on the order of about 250 mW of power, thereby increasing the operating time of the sampling unit for a given battery charge.

20. The active sampler of claim 18, wherein the pump comprises a pair of rotatable members that pump said liquid flow by rotating at different rates in the same direction.

21. The active sampler of claim 10, wherein each of the first and second flow path sections have no valves disposed between the inlet and one end of the sampling unit and no valves disposed between another end of the sampling unit and the outlet.

22. The active sampler of claim 18, wherein each of the first and second flow path sections have no valves disposed between the inlet and one end of the sampling unit and no valves disposed between another end of the sampling unit and the outlet.

* * * * *

UNITED STATES PATENT AND TRADEMARK OFFICE
CERTIFICATE OF CORRECTION

PATENT NO. : 8,119,065 B2
APPLICATION NO. : 12/173612
DATED : February 21, 2012
INVENTOR(S) : William D. Bowers and Gregory F. Quinn It is certified that error appears in the above-identified patent and that said Letters Patent is hereby corrected as shown below:

In the Specification:

At column 5, line 63, please delete "geneva" and insert --Geneva--, therefor.

In the Claims:

In Claim 11, at column 12, line 1, please delete "The system of claim" and insert --The active sampler of claim--, therefor.

In Claim 19, at column 12, line 46, please delete "The system of claim" and insert --The active sampler of claim--, therefor.

Signed and Sealed this
Twenty-fourth Day of September, 2013

Teresa Stanek Rea
*Deputy Director of the United States Patent and Trademark Office*